(12) United States Patent
Ueno

(10) Patent No.: US 8,962,688 B2
(45) Date of Patent: Feb. 24, 2015

(54) METHOD FOR THE TREATMENT OF GASTROINTESTINAL DISORDERS

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 347 days.

(21) Appl. No.: 11/401,382

(22) Filed: Apr. 11, 2006

(65) Prior Publication Data

US 2007/0276006 A1   Nov. 29, 2007

Related U.S. Application Data

(60) Provisional application No. 60/670,238, filed on Apr. 12, 2005.

(51) Int. Cl.
*A61K 31/5575* (2006.01)
*A61K 31/4439* (2006.01)

(52) U.S. Cl.
CPC ......... *A61K 31/4439* (2013.01); *A61K 31/5575* (2013.01)
USPC .......................................... 514/573; 514/338

(58) Field of Classification Search
None
See application file for complete search history.

(56) References Cited

U.S. PATENT DOCUMENTS

| | | | |
|---|---|---|---|
| 5,073,569 A | 12/1991 | Ueno et al. |
| 5,166,174 A | 11/1992 | Ueno et al. |
| 5,212,324 A | 5/1993 | Ueno |
| 5,221,763 A | 6/1993 | Ueno et al. |
| 5,225,439 A | 7/1993 | Ueno et al. |
| 5,284,858 A | 2/1994 | Ueno et al. |
| 5,317,032 A | 5/1994 | Ueno et al. |
| 5,380,709 A | 1/1995 | Ueno et al. |
| 5,428,062 A | 6/1995 | Ueno et al. |
| 5,739,161 A | 4/1998 | Ueno |
| 5,886,034 A | 3/1999 | Ueno et al. |
| 6,242,485 B1 | 6/2001 | Ueno |
| 6,265,440 B1 | 7/2001 | Ueno et al. |
| 6,414,016 B1 | 7/2002 | Ueno |
| 6,583,174 B1 | 6/2003 | Ueno et al. |
| 2003/0119898 A1 | 6/2003 | Ueno et al. |
| 2003/0130352 A1 | 7/2003 | Ueno et al. |
| 2003/0166632 A1 | 9/2003 | Ueno |
| 2004/0138308 A1 | 7/2004 | Ueno et al. |

FOREIGN PATENT DOCUMENTS

| | | |
|---|---|---|
| WO | WO 00/35448 A1 | 6/2000 |
| WO | WO 2004/060377 A1 | 6/2004 |
| WO | 2004/064719 A2 | 8/2004 |
| WO | 2004/073654 A2 | 9/2004 |

OTHER PUBLICATIONS

Vanderhoff et al., American Family Physician, 2002, vol. 66(2), pp. 273-280.*
André Robert; Prostaglandins and the Gastrointestinal Tract; Raven Press, New York 1981, Chapter 57, p. 1406-1434.
D.S. Rampton; Prostanoids and intestinal physiology; Prostglandins: Biology and Chemistry of Prostglandins and Related Eicosanoids; 323-344 (Churchill Livingstone, 1988).
C.J. Hawkey and D.S. Rampton; Prostaglandins and the Gastrointestinal Mucosa: Are They Important in Its Function, Disease, or Treatment?, Gastroenterology, 1985, 89: 1162-88.
Charles E. Eberhart and Raymond N. Dubois; Eicosanoids and the Gastrointestinal Tract; Gastroenterology 1995; 109:285-301.
André Robert; Antisecretory, Antiulcer, Cytoprotective and Diarrheogenic Properties of Prostaglandins; Advances in Prostglandin and Thromboxane Research, vol. 2, 1976, p. 507-520.
I.H.M. Main; Pharmacology of prostaglandins; Postgraduate Medical Journal (1988) 64 (Suppl. 1), 3-6.
Kenton M. Sanders; Role of prostaglandins in regulating gastric motility; American Physiological Society, 1984, G177-G126.
M. Pairet, T. Bouyssou, and Y. Ruckebusch; American Physiological Society, 1986, G302-G308.
Timothy S. Gaginella; Eicosanoid-Mediated Intestinal Secretion; Textbook of Secretory Diarrhea; Raven Press, New York, 1990, 14-30.
Jon P. Monk and Stephen P. Clissod; Misoprostol A Preliminary Review of Its Pharmacodynamic and Pharmacokinetic Properties, and Therapeutic Efficacy in the Treatment of Peptic Ulcer Disease; ADIS Press Limited, Drugs 33: 1-30 (1987).
Nathaniel F. Pierce MD, Charles C.J. Carpenter, Jr. MD, Herbert L. Elliott MD, and William B. Greenough, III, MD; Effects of Prostaglandins, Theophylline, and Cholera Exotoxin upon Transmucosal Water and Electrolyte Movement in the Canine Jejunum; Gastroenterology, vol. 60, No. 1, 1971, p. 22-32.
Eckhard Beubler, Klaus Bukhave and JØrgen Rask-Madsen; Significance of Calcium for the Prostaglandin $E_2$-Mediated Secretory Response to 5-Hydroxytryptamine in the Small Intestine of the Rat In Vivo; Gastroenterology 1986; 90: 1972-7.
L.L. Clarke and R.A. Argenzio; NaCl transport across equine proximal colon and the effect of endogenous prostanoids; American Physiological Society, 1990, p. G62-G69.
J.M. Hunt & E.L. Gerring; The effect of prostaglandin $E_1$ on mobility of the equine gut; J. Vet. Pharmacol. Therap. 8, 165-173, 1985.
Esam Z. Dajani, Erik A.W. Roge and Ralph E. Bertermann; Effects of E Prostaglandins, Diphenoxylate and Morphine on Intestinal Motility in Vivo; European Journal of Pharmacology, 34 (1975) 105-113.
Joseph H. Selin; Intestinal Electrolyte Absorption and Secretion; Gastrointestinal and Liver Disease: Pathophysiology, Diagnosis, and Management 1451-1471 (WB Saunders Company, 1988).
J.L. Wallace & A.W. Tigley; Review article: new insights into prostaglandins and mucosal defence; Aliment Pharmacol Ther 1995: 9: 227-235.
A. Goszcz, K. Bieron, & L. Grodzinska; Misoprostol As Agonist of $IP_2$ Receptor; Journal of Physiology and Pharmacology, 2002, 53, 4, pp. 635-641.
Lee J. Hixson et al., "Current Trends in the Pharmacotherapy for Peptic Ulcer Disease"; Arch. Intern. Med., vol. 152, No. 4, pp. 726-732 (Apr. 1992).
Yukihiro Sakurai; medicina, 1999, vol. 36, No. 9, p. 1526-1528.
Tsuyoshi Yabana, et al., Rinsyo to Kenkyu, 1998, vol. 75, No. 2, p. 231-241.
Tomoyuki Yoneta, et al., Yakuri to Chiryo, 1995, vol. 23, No. 7, p. 17-23.
Yoshihisa Tsukamoto, et al., Yakuri to Chiryo, 1996, vol. 24, No. 9, p. 133-148.
Konnichi-No-Chiryouyaku (Today's therapeutic agent), Explanation and Handbook 2000, edited by Yutaka Mizushima; p. 655-657, 670-671.

* cited by examiner

*Primary Examiner* — Savitha Rao
*Assistant Examiner* — Gregg Polansky
(74) *Attorney, Agent, or Firm* — Sughrue Mion, PLLC

(57) ABSTRACT

The present invention relates to combined use of (a) a specific prostaglandin (PG) compound and (b) a $H^+,K^+$-ATPase inhibitor for the treatment of gastrointestinal disorders.

14 Claims, 1 Drawing Sheet

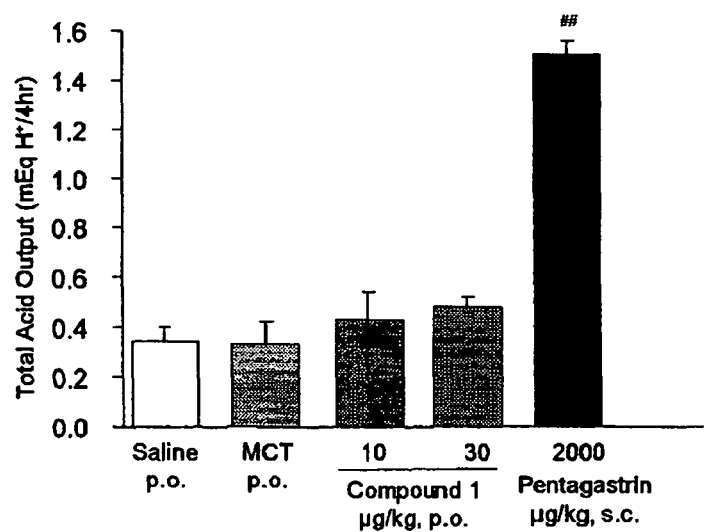

METHOD FOR THE TREATMENT OF GASTROINTESTINAL DISORDERS

CROSS-REFERENCE TO RELATED APPLICATIONS

This application claims the benefit of provisional application No. 60/670,238 filed Apr. 12, 2005, the contents of which are herein incorporated by reference.

TECHNICAL FIELD

The present invention relates to a pharmaceutical composition comprising a specific prostaglandin compound and a $H^+,K^+$-ATPase inhibitor and method for treating gastrointestinal disorders in a mammalian subject using the composition.

BACKGROUND ART

Proton pump inhibitors (PPI) are potent inhibitors of gastric acid secretion by inhibiting $H^+,K^+$-ATPase, the enzyme involved in the final step of hydrogen ion production in the parietal cells, and highly effective in the treatment of gastric acid related diseases such as gastric ulcer, bleeding ulcer, duodenal ulcer, NSAID-induced ulcer, peptic ulcer, erosive esophagitis, gastroesophageal reflux disease, *Helicobacter pylori* infections, Zollinger-Ellison syndrome, NSAID or COX2 inhibitor-associated prophylaxis, Dyspepsia and gastritis in humans. There are currently five different PPIs available including omeprazole, lansoprazole, rabeprazole, esomeprazole and pantoprazole. These agents are all substituted benzimidazoles that inhibit final common pathway of gastric acid secretion.

Gastroesophageal reflux refers to the retrograde movement of gastric contents from the stomach into the esophagus. When this reflux leads to symptomatic conditions or histologic alterations, it is known as gastroesophageal reflux disease (GERD). The reflux of the gastric material into the esophagus may lead to inflammation, hyperplasia of the esophageal lining, esophageal ulcers and Barrett's esophagus. GERD is usually a chronic, relapsing condition. Approximately 44% of the adult US population experiences heartburn at least monthly, 18% experience heartburn at least twice weekly, and 7% experience heartburn daily. Approximately one million Americans have erosive esophagitis, and as many as 20% of these individuals develop complications like esophageal strictures. Therapy for GERD is directed at eliminating the patient's symptoms, decreasing the frequency and duration of reflux, healing the injured mucosa and preventing the development of complications. The management of GERD includes lifestyle modification, acid suppression therapy, and possibly surgery. Lifestyle modifications include elevation of, the head of the bed, dietary changes, smoking cessation and weight loss. Proton pump inhibitors are the mainstay of acid suppression therapy for GERD.

Peptic ulcer disease is also a chronic disease typified by exacerbations and remissions. About 10% of all Americans will develop a peptic ulcer during their lifetime. Duodenal ulcer is more common than gastric ulcer. Duodenal ulcer usually occurs in individuals between 25 and 55 years old whereas gastric ulcer most often occurs in individuals between 55 and 65 years old. Peptic ulcers develop from abnormalities in acid secretion, mucosal defense and motility. *Helicobacter pylori* and nonsteroidal antiinflammatory medications also play an important role in the development of ulcer disease. Drug therapy for peptic ulcer disease is aimed at reducing gastric acidity and enhancing mucosal defense.

Zollinger-Ellison syndrome (ZES) is an acid hypersecretory state caused by a gastrin secreting tumor in the pancreas. ZES occurs in about 0.1% of patients with duodenal ulcer. It is diagnosed when patients have a basal acid output greater than 15 meq/hr. Proton pump inhibitors are the drugs of choice for the management of ZES.

The proton pump inhibitors are the most effective acid suppression drugs available. All five of the available agents appear to be equally efficacious for treating GERD, gastric ulcer and duodenal ulcer. However it is reported that esomeprazole 40 mg was more effective in controlling acid secretion than omeprazole 40 mg, pantoprazole 40 mg or lansoprazole 30 ng (Medical Letter vol. 43 (W1103B), 2001). Because pantoprazole and rabeprazole tablets cannot be crushed or made into a suspension formulation, these two PPIs are not well-suited to pediatric patients or patients with swallowing difficulties (CIGNA HEALTHCARE COVERAGE POSITION Number 4005).

Prostaglandins (hereinafter, referred to as PGs) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

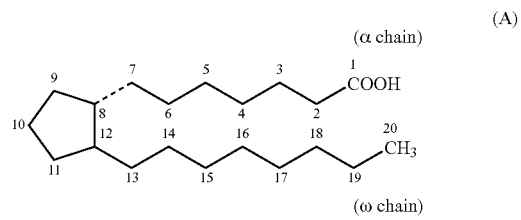

PGs are classified into several types according to the structure and substituents on the five-membered ring, for example, Prostaglandins of the A series (PGAs);

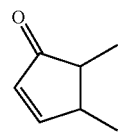

Prostaglandins of the B series (PGBs);

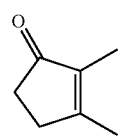

Prostaglandins of the C series (PGCs);

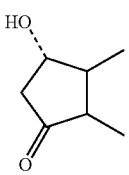

Prostaglandins of the D series (PGDs);

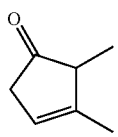

Prostaglandins of the E series (PGEs);

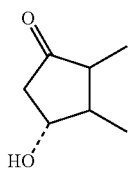

Prostaglandins of the F series (PGFs);

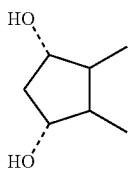

and the like. Further, they are classified into $PG_1$s containing a 13,14-double bond; $PG_2$s containing, 5,6- and 13,14-double bonds; and $PG_3$s containing 5,6-, 13,14- and 17,18-double bonds. PGs are known to have various pharmacological and physiological activities, for example, vasodilatation, inducing of inflammation, platelet aggregation, stimulating uterine muscle, stimulating intestinal muscular activity, anti-ulcer effects and the like. The major prostaglandins produced in the human gastrointestinal (GI) system are those of the E, I and F series (Sellin, Gastrointestinal and Liver Disease: Pathophysiology, Diagnosis, and Management. (WB Saunders Company, 1998); Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., Gastroenterology, 109: 285-301 (1995), the cited references are herein incorporated by reference).

Under normal physiological conditions, endogenously produced prostaglandins play a major role in maintaining GI function, including regulation of intestinal motility and transit, and regulation of fecal consistency. (Sellin, Gastrointestinal and Liver Disease: Pathophysiology, Diagnosis, and Management. (WB Saunders Company, 1998); Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1-988), Hawkey, et al., *Gastroenterology*, 89: 1162-1188 (1985); Eberhart, et al., *Gastroenterology*, 109: 285-301 (1995); Robert, *Adv Prostaglandin Thromboxane Res*, 2:507-520 (1976); Main, et al., *Postgrad Med J*, 64 Suppl 1: 3-6 (1988); Sanders, *Am J Physiol*, 247: G117 (1984); Pairet, et al., *Am J Physiol.*, 250 (3 pt 1): G302-G308 (1986); Gaginella, Textbook of Secretory Diarrhea 15-30 (Raven Press, 1990)). When administered in pharmacological doses, both $PGE_2$ and $PGF_{2\alpha}$ have been shown to stimulate intestinal transit and to cause diarrhea (Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Robert, *Adv Prostaglandin Thromboxane Res*, 2:507-520 (1976)). Furthermore, the most commonly reported side effect of misoprostol, a $PGE_1$ analogue developed for the treatment of peptic ulcer-disease, is diarrhea (Monk, et al., Drugs 33 (1): 1-30 (1997)) The references cited in this paragraph are herein incorporated by reference.

PGE or PGF can stimulate intestinal contraction, but the enteropooling effect is poor. Accordingly, it is impractical to use PGEs or PGFs as cathartics because of side effects such intestinal contraction that cause abdominal pain.

Multiple mechanisms, including modifying enteric nerve responses, altering smooth muscle contraction, stimulating mucous secretion, stimulating cellular ionic secretion (in particular electrogenic $Cl^-$ transport) and increasing intestinal fluid volume have been reported to contribute to the GI effects of prostaglandins (Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., Gastroenterology, 109: 285-301 (1995); Robert, *Adv Prostaglandin Thromboxane Res*, 2:507-520 (1976); Main, et al., Postgrad Med J, 64 Suppl 1: 3-6 (1988); Sanders, *Am J Physiol*, 247: G117 (1984); Pairet, et al., *Am J Physiol*, 250 (3 pt 1): G302-G308 (1986); Gaginella, Textbook of Secretory Diarrhea 15-30 (Raven Press, 1990); Federal Register Vol. 50, No. 10 (GPO, 1985); Pierce, et al., *Gastroenterology* 60 (1): 22-32 (1971); Beubler, et al., *Gastroenterology*, 90: 1972 (1986); Clarke, et al., *Am J Physiol* 259: G62 (1990); Hunt, et al., *J Vet Pharmacol Ther*, 8 (2): 165-173 (1985); Dajani, et al., *Eur J Pharmacol*, 34(1): 105-113 (1975); Sellin, Gastrointestinal and Liver Disease: Pathophysiology, Diagnosis, and Management 1451-1471 (WB Saunders Company, 1998)). Prostaglandins have additionally been shown to have cytoprotective effects (Sellin, Gastrointestinal and Liver Disease Pathophysiology, Diagnosis, and Management. (WB Saunders Company, 1998); Robert, *Physiology of the Gastrointestinal Tract* 1407-1434 (Raven, 1981); Robert, *Adv Prostaglandin Thromboxane Res* 2:507-520 (1976); Wallace, et al., Aiiment Pharmacol Ther 9: 227-235 (1995)). The references cited in this paragraph are herein incorporated by reference.

U.S. Pat. Nos. 5,225,439, 5,166,174, 5,284,858, 5,428,062, 5,380,709, 5,886,034 and 6,265,440 (the cited patents are herein incorporated by reference) describe that certain prostaglandin E compounds are effective for the treatment of ulcers such as duodenal ulcer and gastric ulcer.

U.S. Pat. No. 5,317,032 to Ueno et al describes prostaglandin analog cathartics, including the existence of bicyclic tautomers and U.S. Pat. No. 6,414,016 to Ueno describes the bicyclic tautomers as having pronounced activity as anti-constipation agents (the cited patents are herein incorporated by reference). The bicyclic tautomers, substituted by one or more halogen atoms can be employed in small doses for relieving constipation. At the C-16 position, especially, fluorine atoms, can be employed in small doses for relieving constipation.

U.S. Patent publication No. 2003/0130352 to Ueno et al (the cited publication is herein incorporated by reference) describes prostaglandin compound opens and activates chloride channels, especially ClC channels, more especially ClC-2 channel.

U.S Patent publication No. 2003/0166632 to Ueno (the cited publication is herein incorporated by reference) described ClC-2 channel opener is effective for the treatment of a disease or a condition responsive to opening of ClC-2 channel.

U.S. Patent publication No. 2003/0119898 to Ueno et al (the cited publication is herein incorporated by reference) describes specific composition of a halogenated prostaglandin analog for the treatment and prevention of constipation.

U.S. Patent publication No. 2004/0138308 to Ueno et al (the cited publication is herein incorporated by reference) describes chloride channel opener, especially a prostaglandin compound for the treatment of abdominal discomfort, and the treatment of functional gastrointestinal disorders such as irritable bowel syndrome and functional dyspepsia.

International Publication No. WO00/35448 (the cited publication is herein incorporated by reference) describes a pharmaceutical formulation comprising a proton pump inhibitor and specific gastric antisecretory prostaglandin analogue for use in the treatment of gastrointestinal disorders.

It is reported that misoprostol, one of the gastric antisecretory prostaglandin analogue inhibits platelet aggregation (Journal of Physiology and Pharmacology 2002, 53, 4, 635-641). It is also reported that ornoprostil, one of the gastric antisecretory prostaglandin analogue, has an anti-platelet agglutination effect to enhance the bleeding, so it should be carefully administered to the patient with hemorrhagic ulcer (ornoprostil package insert). The cited references are herein incorporated by reference.

DISCLOSURE OF THE INVENTION

An object of the present invention is to provide a novel combination of known compounds useful for treating gastrointestinal disorders. In other wards, an object of the present invention is to provide a novel composition useful for treating gastrointestinal disorders. Another object of the present invention is to provide a method for treating gastrointestinal disorders.

The present invention relates to a pharmaceutical composition comprising:

(a) a pharmaceutically effective amount of a prostaglandin (PG) compound represented by the formula (I):

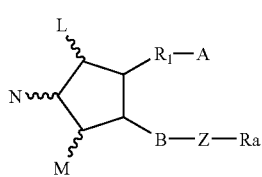

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

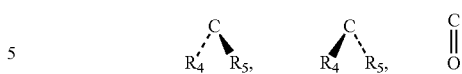

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group, provided that Ra is substituted by halogen and/or Z is C=O, (b) a pharmaceutically effective amount of a H$^+$, K$^+$-ATPase inhibitor and a pharmaceutically suitable excipient. The composition is useful for the treatment of gastrointestinal disorders.

The present invention also relates to a method for treating gastrointestinal disorders in a mammalian subject, which comprises administering to the subject in need thereof, a combination of (a) a pharmaceutically effective amount of a prostaglandin (PG) compound represented by the formula (I) and (b) a pharmaceutically effective amount of a H$^+$, K$^+$-ATPase inhibitor.

The present invention further relates to a combined use of (a) a prostaglandin (PG) compound represented by the formula (I) and (b) a H$^+$, K$^+$-ATPase inhibitor for manufacturing a pharmaceutical composition for the treatment of gastrointestinal disorders in a mammalian subject.

BRIEF DESCRIPTION OF THE DRAWINGS

FIG. 1 is a graph showing the effects of 13,14-dihydro-15-keto-16,16-difluoro-PGE1 (Compound 1) on total acid output in rats. Values are Means±S.E. of 6 animals. ##p<0.01 compared to salin-treated control group by Student's t-test.

DETAILED DESCRIPTION OF THE INVENTION (a) The Compound of Formula (I)

The nomenclature of the prostaglandin compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-deoxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substuents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A specific prostaglandin compound used in the present invention is represented by the formula (I):

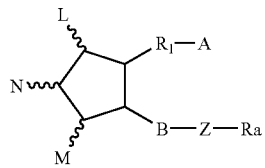

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

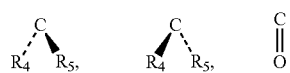

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, provided that Ra is substituted by halogen and/or Z is C=O.

A preferred compound used in the present invention is represented by the formula (II):

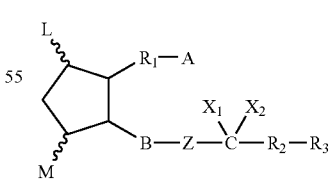

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

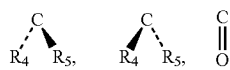

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

X$_1$ and X$_2$ are hydrogen, lower alkyl, or halogen;

R$_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

R$_2$ is a single bond or lower alkylene; and

R$_3$ is lower alkyl, lower alkoxy, lower alkanoyloxy, cyclo(lower)alkyl, cyclo(lower)alkyloxy, aryl, aryloxy, heterocyclic group or heterocyclic-oxy group, provided that one of X$_1$ and X$_2$ is substituted by halogen and/or Z is C=O.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydrogen, hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:
—$CH_2$—$CH_2$—$CH_2$—$CH_2$—$CH_2$—$CH_2$—,
—$CH_2$—$CH$=$CH$—$CH_2$—$CH_2$—$CH_2$—,
—$CH_2$—$CH_2$—$CH_2$—$CH_2$—$CH$=$CH$—,
—$CH_2$—$C$≡$C$—$CH_2$—$CH_2$—$CH_2$—,
—$CH_2$—$CH_2$—$CH_2$—$CH_2$—$O$—$CH_2$—,
—$CH_2$—$CH$=$CH$—$CH_2$—$O$—$CH_2$—,
—$CH_2$—$C$≡$C$—$CH_2$—$O$—$CH_2$—,
—$CH_2$—$CH_2$—$CH_2$—$CH_2$—$CH_2$—$CH_2$—$CH_2$—,
—$CH_2$—$CH$=$CH$—$CH_2$—$CH_2$—$CH_2$—$CH_2$—,
—$CH_2$—$CH_2$—$CH_2$—$CH_2$—$CH_2$—$CH$=$CH$—,
—$CH_2$—$C$≡$C$—$CH_2$—$CH_2$—$CH_2$—$CH_2$—,
—$CH_2$—$CH_2$—$CH_2$—$CH_2$—$CH(CH_3)$—$CH_2$—,
—$CH_2$—$CH_2$—$CH_2$—$CH_2$—$CH(CH_3)$—$CH_2$—,
$CH_2$—$CH_2$—$CH_2$—$CH_2$—$CH_2$—$CH_2$—$CH_2$—$CH_2$—,
—$CH_2$—$CH$=$CH$—$CH_2$—$CH_2$—$CH_2$—$CH_2$—$CH_2$—,
—$CH_2$—$CH_2$—$CH_2$—$CH_2$—$CH_2$—$CH_2$—$CH$=$CH$—,
—$CH_2$—$C$≡$C$—$CH_2$—$CH_2$—$CH_2$—$CH_2$—$CH_2$—, and
—$CH_2$—$CH_2$—$CH_2$—$CH_2$—$CH_2$—$CH_2$—$CH(CH_3)$—$CH_2$—.

Preferred Ra is a hydrocarbon containing 1-10 carbon atoms, more preferably, 1-8 carbon atoms. Ra may have one or two side chains having one carbon atom.

Most preferred embodiment is a prostaglandin compound is 13,14-dihydro-15-keto-16,16-difluoro-prostaglandin $E_1$ compound or 13,14-dihydro-15-keto-16,16-difluoro-18-methyl-prostaglandin $E_1$ compound.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the PG compound which is dihydro between 13 and 14, and keto($=$O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

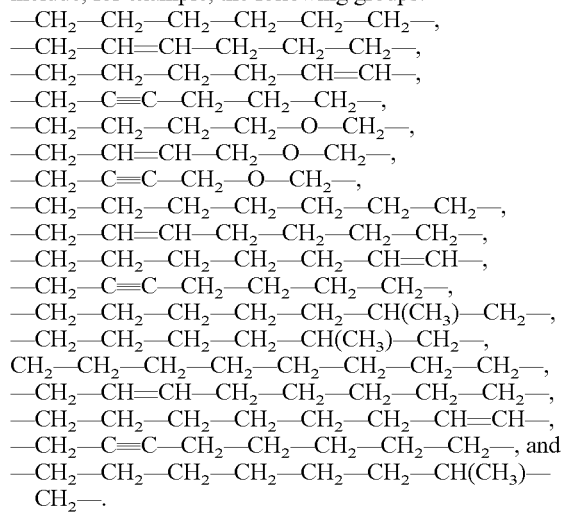

wherein, A is —$CH_3$, or —$CH_2OH$, —$COCH_2OH$, —COOH or a functional derivative thereof;

$X_1'$ and $X_2'$ are hydrogen, lower alkyl, or halogen;

Y is

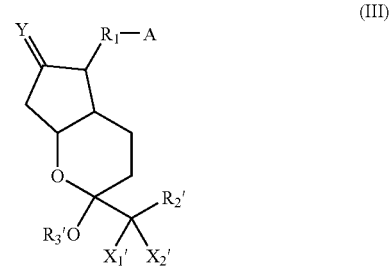

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited patents are herein incorporated by reference).

(b) $H^+,K^+$-ATPase inhibitor $H^+,K^+$-ATPase inhibitors, i.e. proton pump inhibitors used in the present invention include, but not limited to, the compounds of the general formula (II), an alkaline salt thereof, one of the single enantiomers thereof or an alkaline salt of one of the enantiomers:

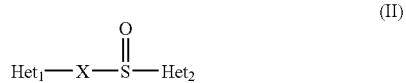
(II)

wherein,
$Het_1$ is

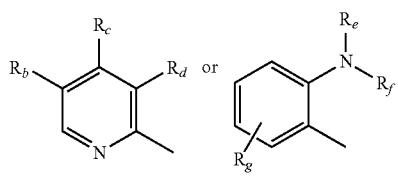

wherein $R_b$, $R_c$ and $R_d$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy, $R_e$ and $R_f$ are the same or different and selected from hydrogen, alkyl and arylalkyl, and $R_g$ is hydrogen, halogen, trifluoromethyl, alkyl or alkoxy;
$Het_2$ is

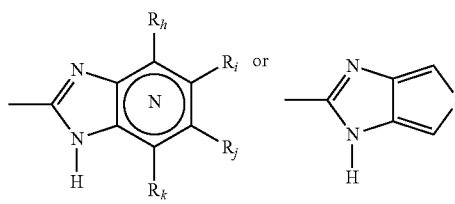

wherein $R_h$-$R_k$ are the same or different and selected from hydrogen, alkyl, alkoxy, halogen, haloalkoxy, alkylcarbonyl, alkoxycarbonyl, oxazolinyl, trifluoroalkyl, or adjacent groups $R_h$-$R_k$ form ring structures which may be further substituted, and N in the center of the benzene ring of the benzimidazole moiety means that one of the ring carbon atoms substituted by $R_h$-$R_k$ optionally may be exchanged for a nitrogen atom without any substituents; and X is

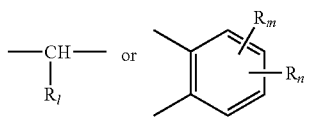

wherein $R_l$ is hydrogen or forms an alkylene chain together with $R_d$, and $R_m$ and $R_n$ are the same or different and selected from hydrogen, halogen or alkyl.

Examples of specifically preferred compounds according to formula II are

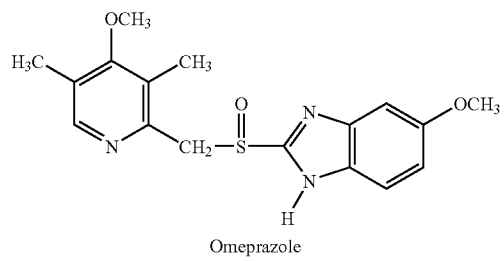
Omeprazole

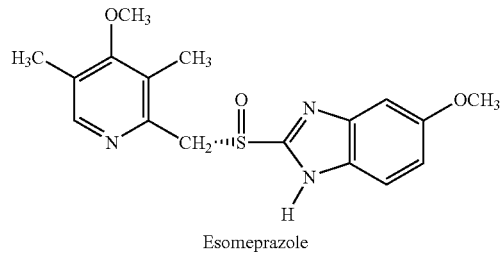
Esomeprazole

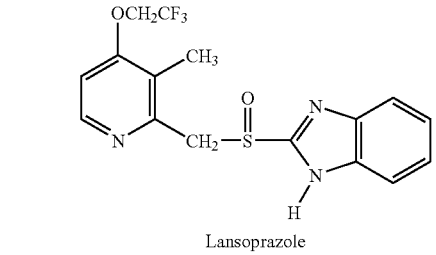
Lansoprazole

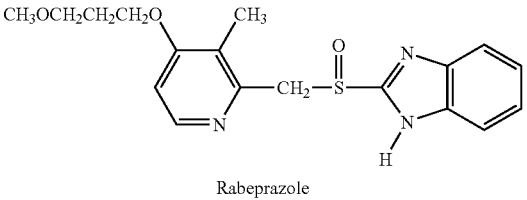
Rabeprazole

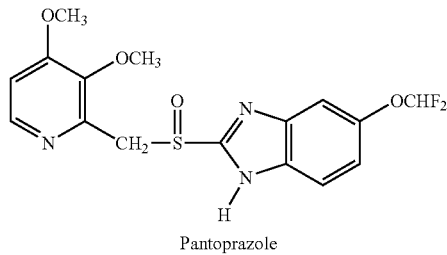
Pantoprazole

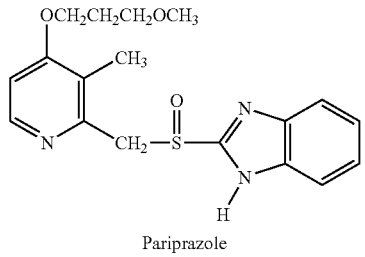
Pariprazole

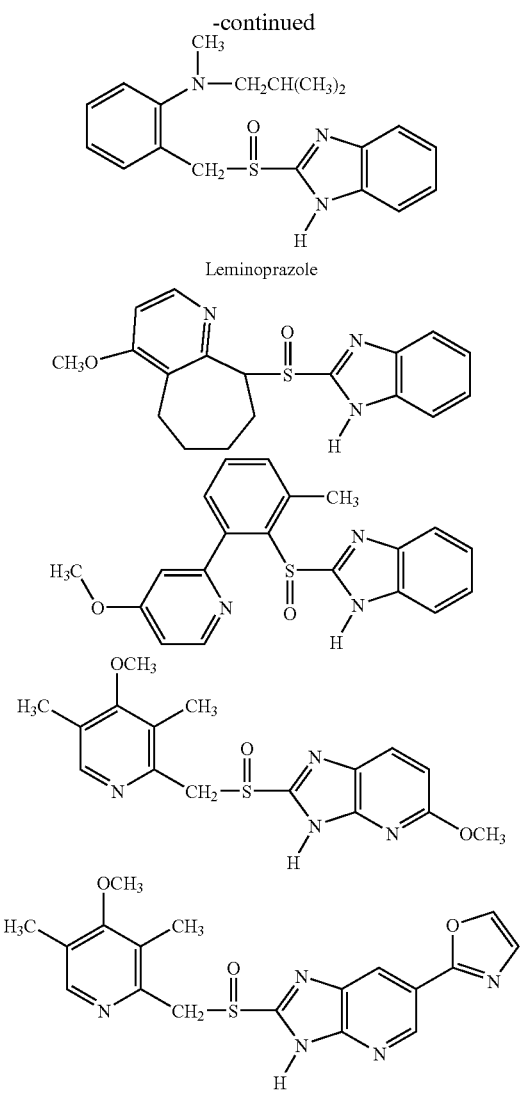

The compounds used herein may be used in neutral form or in the form of an alkaline salt, such as for instance the $Mg^{2+}$, $Ca^{2+}$, $Na^{2+}$ or $K^+$ salts. The compounds may also be used in the form of one of its single enantiomers or an alkaline salt of the single enantiomer.

Preferred compounds of the proton pump inhibitors used herein are omeprazole, lansoprazole, pantoprazole, esomeprazole, rabeprazole or a pharmaceutically acceptable salt thereof, one of its single enantiomers or a pharmaceutically acceptable salt thereof, especially, omeprazole, lansoprazole and esomeprazole magnesium, more especially, omeprazole and lansoprazole.

The Pharmaceutically Suitable Excipient

According to the invention, the composition may be formulated in any form. The pharmaceutically suitable excipient may be, therefore, selected depending on the desired form of the composition. According to the invention, "pharmaceutically suitable excipient" means an inert substance, which is suitable for the form, combined with the active ingredient of the invention.

For example, solid composition for oral administration of the present invention may include tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrant such as fibrous calcium gluconate; stabilizer such as cyclodextrin, for example, α,β- or γ-cyclodextrin; etherified cyclodextrin such as dimethyl-α-, dimethyl-β-, trimethyl-β-, or hydroxypropyl-β-cyclodextrin; branched cyclodextrin such as glucosyl-, maltosyl-cyclodextrin; formylated cyclodextrin, cyclodextrin containing sulfur; phospholipid and the like. When the above cyclodextrins are used, an inclusion compound with cyclodextrins may be sometimes formed to enhance stability. Alternatively, phospholipid may be sometimes used to form a liposome, resulting in enhanced stability.

Tablets or pills may be coated with film soluble in the stomach or intestine such as sugar, gelatin, hydroxypropyl cellulose, or hydroxypropylmethyl cellulose phthalate as needed. Further, they may be formed as capsules with absorbable substances such as gelatins. Preferably, the composition is formulated in a soft gelatin capsule with liquid contents of the specific prostaglandin compound and a medium chain fatty acid triglyceride. Examples of the medium chain fatty acid triglyceride used in the present invention include a triglyceride of a saturated or unsaturated fatty acid having 6-14 carbon atoms which may have a branched chain. A preferred fatty acid is a straight chain saturated fatty acid, for example caproic acid (C6), caprylic acid (C8), capric acid (C10), lauric acid (C12) and myristic acid (C14). In addition, two or more medium chain fatty acid triglycerides may be used in combination. Further suitable excipients are disclosed in U.S. Pat. No. 6,583,174 (the cited patent is herein incorporated by reference).

A liquid composition for oral administration may be pharmaceutically acceptable emulsion, solution, suspension, syrup, or elixir, as well as generally used inactive diluent. Such composition may contain, in addition to the inactive diluent, adjuvants such as lubricants and suspensions, sweetening agents, flavoring agents, preservatives, solubilizers, anti-oxidants and the like. The details of the additives may be selected from those described in any general textbooks in the pharmaceutical field. Such liquid compositions may be directly enclosed in soft capsules. Solutions for parenteral administration, for example, suppository, enema and the like according to the present invention include sterile, aqueous or non-aqueous solution, suspension, emulsion, detergent and the like. The aqueous solution and suspension includes, for example, distilled water, physiological saline and Ringer's solution.

The non-aqueous solution and suspension include, for example, propylene glycol, polyethylene glycol, fatty acid triglyceride, and vegetable oil such as olive oil, alcohols such as ethanol, polysorbate and the like. Such composition may contain adjuvants such as preservatives, wetting agent, emulsifier, dispersant, anti-oxidants and the like.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

Another form of the present composition is suppository or pessary, which may be prepared by mixing active ingredients into a conventional base such as cacao butter that softens at body temperature, and nonionic surfactants having suitable softening temperatures may be used to improve absorbability.

According to the method of the invention, the composition of the present invention can be administered systemically or locally by means of oral or parental administration, including a suppository, enema and the like. Single or multiple compositions may be administered to achieve the desired dose.

According to the present invention, a mammalian subject may be treated by the instant invention by administering the combination of the compounds specified in the present invention. The mammalian subject may be any subject including a human. The compounds may be applied systemically or topically. Usually, the compounds may be administered by oral administration, intravenous injection (including infusion), subcutaneous injection, intra rectal administration, intra vaginal administration, transdermal administration and the like. The dose may vary depending on the strain of the animal, age, body weight, symptom to be treated, desired therapeutic effect, administration route, term of treatment and the like. For example, a satisfactory effect can be obtained by systemic administration 1-6, preferably-1-4 times per day or continuous administration of a combination of 0.001-100000 µg, preferably 0.01-10000 µg, more preferably 0.1-1000 µg and especially 1-100 µg of the specific prostaglandin compound, and 1-200 mg, more preferably 1-60 mg of $H^+, K^+$-ATPase inhibitor at each dose.

The term "combination" used herein means that the active ingredients, the specific prostaglandin compound and PPI, are both administered to the patient simultaneously in the form of a single entity or dosage, or are both administered to the patient as separate entities either simultaneously or sequentially with no specific time limits, wherein such administration provides therapeutically effective levels of the two components in the body, preferably at the same time.

The term "treatment" used herein includes any means of control such as prevention, care, relief of the condition, attenuation of the condition and arrest of progression.

The specific prostaglandin compounds used herein have a significant antiulcer activity and cytoprotective activity including an activity to induce recovery of barrier function in gastrointestinal tract, and do not substantially affect on the gastric acid output nor ATP-induced platelet agglutination. These facts suggest that the antiulcer activity of the specific prostaglandin compounds is not derived from the inhibition of the gastric acid secretion, which is different of mechanism of action from that of $H^+, K^+$-ATPase inhibitor. Accordingly, the combination has an advantage, by containing the component (a) and (b), that it has a superior effect on the gastrointestinal disorders, thus enabling reduce in dosage, and/or lowering the side-effect.

The "gastrointestinal disorders" used herein include for example, but not limited to, gastric ulcer, bleeding ulcer, duodenal ulcer, NSAID-induced ulcer, peptic ulcer, erosive Esophagitis, Gastroesophageal reflux disease, *Helicobacter pylori* infections, Zollinger-Ellison syndrome, NSAID or COX2 inhibitor-associated prophylaxis, Dyspepsia, gastritis, gastrointestinal bleeding, esophageal ulcers and Barrett's esophagus.

The further details of the present invention will follow with reference to test examples, which, however, are not intended to limit the present invention.

Example 1

Each group of test animals used consisted of 10 male rats of the Crj: Wistar strain. The animals were fasted for 24 hours before the oral administration of the Compound 1 (13,14-dihydro-15-keto-16,16-difluoro-PGE1) or the vehicle. Ten minutes after the oral administration of the test sample or the vehicle, all rats received a 20 mg/kg oral dose of indomethacin. The animals were euthanized 6 hours later. The stomach was removed and the length of the longest axis of each stomach ulcer was measured. The ulcer index was calculated as the sum of the lengths of each individual ulcer.

As shown in Table 1, Compound 1 (13,14-dihydro-15-keto-16,16-difluoro-PGE1) was shown to provide significant protection against indomethacin-induced ulcer formation.

TABLE 1

Effect of Compound 1 on indomethacin-induced stomach ulcers in rats

| Group | Dose (µg/kg, po) | n | Ulcer index$^{a,b}$ | % Inhibition |
|---|---|---|---|---|
| Control (vehicle) | 0 | 10 | 49.6 ± 7.6 | — |
| Compound 1 | 2 | 10 | 27.9 ± 5.1* | 44 |

$^a$Sum of lengths of each individual ulcer
$^b$Mean ± SE;
*p < 0.05 compared to vehicle-treated control group (Student's t-test)

Example 2

Each group of test animals used consisted of 9 or 10 male rats of the Crj: Wistar strain. The animals were fasted for 24 hours before the oral administration of the test sample. Ten minutes after the oral administration of various doses of the Compound 1 (13,14-dihydro-15-keto-16,16-difluoro-PGE1) or the vehicle, each animal was put in a narrow cage, and was immersed in water (23° C.) up to the height of the xipoid process for 6 hours. The animals were then euthanized. The stomach was removed and the maximum length of the longest axis of each stomach ulcer was measured. The ulcer index was calculated as the sum of lengths of each individual ulcer.

As shown in Table 2, Compound 1 was shown to provide protection significantly against stress-induced ulcer formation.

TABLE 2

Effect of Compound 1 on stress-induced stomach ulcers in rats

| Group | Dose (µg/kg, po) | n | Ulcer index$^{a,b}$ | % Inhibition |
|---|---|---|---|---|
| Control (Vehicle) | 0 | 10 | 29.3 ± 3.0 | — |
| Compound 1 | 3 | 10 | 26.6 ± 3.7 | 9.2 |
| Compound 1 | 10 | 9 | 23.4 ± 4.7 | 20.1 |
| Compound 1 | 30 | 10 | 13.4 ± 2.0** | 54.3 |
| Compound 1 | 100 | 10 | 4.3 ± 1.9** | 85.3 |

$^a$Sum of lengths of each individual ulcer
$^b$Mean ± SE;
**p < 0.01 compared to vehicle-treated control group (Dunnett's test)

Example 3

The study was conducted according to the method described by Wong et al (Pharmacol. Soc. 32:49-56, 1989).

Each group of test animals used consisted of 6 male rats of the Crj: Wistar strain. The animals were fasted for 24 hours with free access to water. Each dose formulation of Compound 1 (13,14-dihydro-15-keto-16,16-difluoro-PGE1), saline and medium chain fatty acid triglyceride (MCT) was orally administered 30 minutes before pyloric ligation. For positive control, the animals were received pentagastrin, a known gastric acid stimulator, subcutaneously at 2000 µg/kg. Under ether anesthesia, the abdomen was opened through a midline incision, the pylorus ligated with 3-0 silk suture, and the abdomen closed. The animals were kept without diet and water thereafter. Four hours after pyloric ligation, the animals were euthanized by cervical dislocation and the abdomen opened. The gastric contents were collected into sterile centrifuge tubes, and centrifuged at 3000 rpm for 10 minutes to remove solid materials. The supernatant was collected and the volume measured. A 1 mL aliquot of each gastric fluid sample was titrated to pH 7.0 with 0.01 N sodium hydroxide using an automatic titrater (COMTITE-900, Hiranuma Sangyo, Co., Ltd., Japan) to determine the acidity (mEq $H^+$/mL) Total output of gastric acid for 4 hours was calculated Result The result is shown in FIG. 1. There was no significant difference in total acid output between the saline- and MCT-treated groups. In contrast, subcutaneous dosing of pentagastrin at 2000 µg/kg, which served as a positive control, induced a significant increase compared to the saline-treated control group (p<0.01). The test compound did not affect on the total acid output compared to the vehicle-treated control group.

Example 4

Blood was collected from rabbits of the JW/CSK strain and citrated by mixing with sodium citrate in a ratio of 9 volumes of blood to 1 volume of 3.8% sodium citrate solution. Platelet-rich plasma (PRP) was obtained by centrifugation of the citrated blood at 1000 rpm (168×g) for 10 minutes. After collection of PRP, residual blood was further centrifuged at 3000 rpm (1670×g) for 15 minutes, and the supernatant was used as platelet-poor plasma (PPP). After pre-incubation of PRP (200 µL) with each test solution (25 µL) for 1 minutes at 37° C., 25 µL of platelet aggregation agent (ADP 25 NM) was added. Platelet aggregation was measured with a platelet aggregation meter (HEMATRACER PAT-4A, Niko Bioscience, Inc.). Each test solution was examined with 3 different animal source platelets in duplicate fashion. Inhibition percent was calculated by comparing with the maximal aggregation with the saline-treatment group.

As shown in Table 3, Compound 1 (13,14-dihydro-15-keto-16,16-difluoro-PGE1) had no effect on the platelet aggregation. On the other hand, prostaglandin $E_1$ ($PGE_1$) significantly inhibited the platelet aggregation.

TABLE 3

Effects of Compound 1 and $PGE_1$ on rabbit platelet aggregation induced with ADP

| Test substance | Conc. (g/mL) | n | Maximum aggregation[a] (%) | % Inhibition |
|---|---|---|---|---|
| Control (vehicle) | 0 | 3 | 49.5 ± 3.1 | — |
| Compound 1 | $10^{-7}$ | 3 | 49.5 ± 2.5 | 0 |
| $PGE_1$ | $10^{-7}$ | 3 | 23.3 ± 1.9** | 73 |

[a]Mean ± SE,
**p < 0.01 compared to vehicle control group (Student's t-test)

Example 5

Methods

Wistar rats were used after an overnight fast with free access to water. Compound 1 (13,14-dihydro-15-keto-16,16-difluoro-PGE1) or Compound 2(13,14-dihydro-15-keto-16,16-difluoro-18(s) methyl-$PGE_1$) was orally administered to the animals. When the effect of combined treatment with Compound 1 and proton pump inhibitor (lansoprazole or omeprazole) was evaluated, Compound 1 and proton pump inhibitor were orally administered simultaneously. Control group received the same volume of the vehicle. Ten minutes after the administration, the animals were placed in stress cages and were vertically immersed to the xiphoid process in a water bath maintained at 23° C. Five hours later, each animal was taken out from the cage and sacrificed by $CO_2$ asphyxiation. The stomach was removed after ligating the cardiac region of stomach and the upper part of duodenum. The stomach was filled with 4 mL of physiological saline solution, and fixed in 1% formalin solution for 30 minutes. The stomach was opened along the greater curvature. The length (mm) of the individual ulcer was measured and the ulcer index was expressed as the sum of the lengths of all ulcers per stomach.

(Results)

As shown in Table 4, Compound 1 and 2 inhibited the gastric ulcer in a dose-dependent manner. As shown in Table 5, combined treatment with Compound 1 and lansoprazole inhibited the gastric ulcer more potently as compared to the treatment with lansoprazole alone. Furthermore, combined treatment with Compound 1 and omeprazole also inhibited the gastric ulcer more potently as compared to the treatment with omeprazole alone.

The results demonstrated that the combined treatment with specific prostaglandin compound and proton pump inhibitor had additive and/or synergic effects on the inhibition of gastric ulcer.

TABLE 4

Effects of Compounds 1 and 2 on gastric ulcer induced by water-immersion stress in rats

| Group | n | Dose Route | Ulcer Index[a] Mean ± S.E., mm | Inhibition % |
|---|---|---|---|---|
| Vehicle | 10 | p.o. | 15.9 ± 1.2 | — |
| Compound 1 10 µg/kg | 10 | p.o. | 12.2 ± 1.9 | 23 |
| Compound 1 30 µg/kg | 10 | p.o. | 10.1 ± 1.6 | 36 |
| Compound 1 100 µg/kg | 10 | p.o. | 1.4 ± 0.6 | 91 |
| Compound 2 10 µg/kg | 10 | p.o. | 12.6 ± 2.2 | 21 |
| Compound 2 30 µg/kg | 10 | p.o. | 10.2 ± 2.0 | 36 |
| Compound 2 100 µg/kg | 10 | p.o. | 2.4 ± 0.9 | 85 |

TABLE 5

Effects of combined treatment with Compound 1 and proton pump inhibitor on gastric ulcer induced by water-immersion stress in rats

| Group | n | Dose Route | Ulcer Index[a] Mean ± S.E., mm | Inhibition % |
|---|---|---|---|---|
| Vehicle | 9 | p.o. | 8.6 ± 1.3 | — |
| Lansoprazole 1000 µg/kg | 9 | p.o. | 4.6 ± 1.2 | 46 |
| Lansoprazole 1000 µg/kg + Compound 1 10 µg/kg | 9 | p.o. | 3.7 ± 0.9 | 57 |

TABLE 5-continued

Effects of combined treatment with Compound 1 and proton pump inhibitor on gastric ulcer induced by water-immersion stress in rats

| Group | n | Dose Route | Ulcer Index[a] Mean ± S.E., mm | Inhibition % |
|---|---|---|---|---|
| Omeprazole 3000 μg/kg | 9 | p.o. | 5.9 ± 0.9 | 31 |
| Omeprazole 3000 μg/kg + Compound 1 10 μg/kg | 9 | p.o. | 3.4 ± 1.0 | 60 |

What is claimed is:

1. A method for treating a gastrointestinal disorder in a mammalian subject, which comprises administering to the subject in need thereof, a combination of
    (a) a pharmaceutically effective amount of a prostaglandin (PG) compound of 13,14-dihydro-15-keto-16,16-difluoro-prostaglandin $E_1$ or 13,14-dihydro-15-keto-16,16-difluoro-18-methyl prostaglandin $E_1$, and
    (b) a pharmaceutically effective amount of a $H^+$, $K^+$-ATPase inhibitor of omeprazole or lansoprazole or a pharmaceutically acceptable salt thereof, one of its single enantiomers or a pharmaceutically acceptable salt thereof,
    wherein the gastrointestinal disorder is selected from the group consisting of gastric ulcer, bleeding ulcer, duodenal ulcer, NSAID-induced ulcer, peptic ulcer, erosive esophagitis, gastroesophageal reflux, *Helicobacter pylori* infections in patients having gastric ulcer, Zollinger-Ellison syndrome, gastritis in patients having gastric ulcer, gastrointestinal bleeding caused by gastric ulcers, esophageal ulcers and Barrett's esophagus, and
    wherein the dose of said prostaglandin compound is 1-100 μg and the dose of said $H^+$,$K^+$-ATPase inhibitor is 1-200 mg.

2. The method as described in claim 1, wherein the $H^+$,$K^+$-ATPase inhibitor is omeprazole or a pharmaceutically acceptable salt thereof, one of its single enantiomers or a pharmaceutically acceptable salt thereof.

3. The method as described in claim 1, wherein the $H^+$,$K^+$-ATPase inhibitor is lansoprazole or a pharmaceutically acceptable salt thereof, one of its single enantiomers or a pharmaceutically acceptable salt thereof.

4. The method as described in claim 1, wherein the components (a) and (b) are administered orally.

5. The method of claim 1, wherein the components (a) and (b) are administered simultaneously or sequentially.

6. The method of claim 1, wherein said prostaglandin compound is 13,14-dihydro-15-keto-16,16-difluoro-prostaglandin $E_1$ and the $H^+$,$K^+$-ATPase inhibitor is omeprazole.

7. The method of claim 1, wherein said prostaglandin compound is 13,14-dihydro-15-keto-16,16-difluoro-prostaglandin $E_1$ and the $H^+$, $K^+$-ATPase inhibitor is lansoprazole.

8. The method of claim 1, wherein the dose of said $H^+$, $K^+$-ATPase inhibitor is 1-60 mg.

9. The method of claim 2, wherein the dose of said $H^+$, $K^+$-ATPase inhibitor is 1-60 mg.

10. The method of claim 3, wherein the dose of said $H^+$, $K^+$-ATPase inhibitor is 1-60 mg.

11. The method of claim 1, wherein said prostaglandin compound is 13,14-dihydro-15-keto-16,16-difluoro-18-methyl-prostaglandin $E_1$ and the $H^+$, $K^+$-ATPase inhibitor is omeprazole.

12. The method of claim 1, wherein said prostaglandin compound is 13,14-dihydro-15-keto-16,16-difluoro-18-methyl-prostaglandin $E_1$ and the $H^+$, $K^+$-ATPase inhibitor is lansoprazole.

13. The method of claim 1, wherein the gastrointestinal disorder is selected from the group consisting of gastric ulcer, bleeding ulcer, duodenal ulcer, NSAID-induced ulcer, peptic ulcer, erosive esophagitis, gastroesophageal reflux, Zollinger-Ellison syndrome, esophageal ulcers and Barrett's esophagus.

14. The method of claim 1, wherein the gastrointestinal disorder is gastric ulcer.

* * * * *